(12) United States Patent
Webster, Jr.

(10) Patent No.: US 6,171,275 B1
(45) Date of Patent: Jan. 9, 2001

(54) IRRIGATED SPLIT TIP ELECTRODE CATHETER

(75) Inventor: Wilton W. Webster, Jr., Diamond Bar, CA (US)

(73) Assignee: Cordis Webster, Inc., Diamond Bar, CA (US)

(*) Notice: Under 35 U.S.C. 154(b), the term of this patent shall be extended for 0 days.

(21) Appl. No.: 09/205,116

(22) Filed: Dec. 3, 1998

(51) Int. Cl.[7] .................................................. A61M 1/30
(52) U.S. Cl. ............................ 604/20; 600/374; 607/122
(58) Field of Search ................................. 607/120, 122; 604/19–22; 600/374; 606/41, 50

(56) References Cited

U.S. PATENT DOCUMENTS

| | | | |
|---|---|---|---|
| 2,949,910 | 8/1960 | Brown et al. | 128/2.05 |
| 3,920,021 | 11/1975 | Hiltebrandt | 128/303.17 |
| 4,328,806 | 5/1982 | Cooper | 128/349 B |
| 4,754,752 | 7/1988 | Ginsburg et al. | 128/303.12 |
| 4,848,352 | 7/1989 | Pohndorf et al. | 128/642 |
| 4,960,134 | 10/1990 | Webster, Jr. | 128/786 |
| 5,006,119 | 4/1991 | Acker et al. | 606/27 |
| 5,056,517 | 10/1991 | Fenici | 128/419 P |
| 5,069,674 | 12/1991 | Fearnot et al. | 604/282 |
| 5,211,636 | 5/1993 | Mische | 604/264 |
| 5,281,212 | 1/1994 | Savage et al. | 606/15 |
| 5,313,943 | 5/1994 | Houser et al. | 128/642 |
| 5,334,193 | 8/1994 | Nardella | 606/41 |
| 5,348,554 | 9/1994 | Imran et al. | 606/41 |
| 5,368,564 | 11/1994 | Savage | 604/95 |
| 5,376,083 | 12/1994 | Mische | 604/264 |
| 5,383,852 | 1/1995 | Stevens-Wright | 604/95 |
| 5,383,876 | 1/1995 | Nardella | 606/49 |
| 5,398,683 | 3/1995 | Edwards et al. | 128/642 |
| 5,403,311 | 4/1995 | Abele et al. | 606/49 |
| 5,409,453 | 4/1995 | Lundquist et al. | 604/22 |
| 5,423,811 | 6/1995 | Imran et al. | 606/41 |
| 5,431,168 | 7/1995 | Webster, Jr. | 128/658 |
| 5,431,649 | 7/1995 | Mulier et al. | 606/41 |
| 5,462,521 | 10/1995 | Brucker et al. | 604/20 |
| 5,462,523 | 10/1995 | Samson et al. | 604/30 |
| 5,476,502 | 12/1995 | Rubin | 607/127 |
| 5,500,012 | 3/1996 | Brucker et al. | 607/122 |
| 5,507,725 | 4/1996 | Savage et al. | 604/95 |

(List continued on next page.)

FOREIGN PATENT DOCUMENTS

| | | |
|---|---|---|
| 0571797 | 12/1983 | (EP) . |
| 1690786 | 11/1991 | (SU) . |
| 97/12548 | * 4/1997 | (WO) . |

OTHER PUBLICATIONS

Huang, S.K., et al, "Increase in the Lesion Size and Decrease in the Impedance Rise with a Saline Infusion Electrode Catheter for Radio–frequency Catheter Ablation"; Cardiac Physiol., vol. 80, No. 4, 1291 (Oct. 1989) (abstract).

Wittkampf, F.H. et al, "Radio–frequency Ablation With A Cooled Porous Electrode Catheter", JACC vol. 11, No. 2, Feb. 1988, p. 17A (abstract).

Primary Examiner—Corrine McDermott
(74) Attorney, Agent, or Firm—Christie Parker & Hale, LLP (57) ABSTRACT

An irrigated split tip electrode catheter is provided having a composite tip electrode comprising multiple electrode elements adjacent to each other. A central irrigation channel extends into the composite tip electrode which branches into transverse irrigation channels in each electrode element. An infusion tube extends from a Luer hub at the proximal end of the catheter through the catheter body and into the central irrigation channel of the composite tip electrode. A temperature sensor preferably a thermocouple may be provided for each electrode element. In use, a cooling fluid is passed into and through the infusion tube and through each of the electrode elements to cool the electrode elements and the interface between the electrode elements and the myocardium or blood so as to prevent the formation of coagulum.

34 Claims, 8 Drawing Sheets

U.S. PATENT DOCUMENTS

| | | | |
|---|---|---|---|
| 5,522,815 | 6/1996 | Durgin, Jr. et al. | 606/50 |
| 5,549,108 | 8/1996 | Edwards et al. | 128/642 |
| 5,571,085 | 11/1996 | Accisano, III | 604/95 |
| 5,575,772 | 11/1996 | Lennox | 604/96 |
| 5,584,872 | 12/1996 | LaFontaine et al. | 607/116 |
| 5,643,197 | 7/1997 | Brucker et al. | 604/20 |
| 5,658,278 | 8/1997 | Imran et al. | 606/41 |
| 5,676,693 | 10/1997 | LaFontaine | 607/116 |
| 5,697,927 | 12/1997 | Imran et al. | 606/41 |
| 5,836,875 | 11/1998 | Webster, Jr. | 600/374 |
| 5,843,076 | 12/1998 | Webster, Jr. et al. | 606/41 D |

\* cited by examiner

IRRIGATED SPLIT TIP ELECTRODE CATHETER

FIELD OF THE INVENTION

This invention relates to electrophysiology catheters and more particularly to an irrigated split-tip electrode catheter for use in electrocardiology ablation and mapping procedures.

BACKGROUND OF THE INVENTION

The heart has a natural pacemaker and conduction system which causes the heart muscle to contract, or beat, in an orderly rhythmical manner. The normal pacing rate for an adult at rest is about 60 to 70 beats per minute. There are many physiologic abnormalities which cause one or more chambers of the heart to beat more rapidly (tachycardia or flutter) or chaotically (fibrillation). A patient cannot live with ventricular fibrillation because there would be no blood pumped through the arteries, but may live with atrial fibrillation so long as the chaotic impulses are filtered out at the AV node and do not reach the ventricals. A patient may also live with atrial flutter and various forms of tachycardia but quality of life may be considerably compromised.

Many of these arrhythmias can be treated effectively by ablation using radio-frequency (RF) energy. Other arrhythmias are less effectively treated, requiring more RF lesions for a successful outcome or resulting in no successful outcome. RF ablation is performed with a catheter having one or more electrodes which deliver the RF energy to the cardiac tissue. In operation the catheter is guided through a vein or artery into the heart chamber and positioned at one or more sites, determined by an electrophysiologist, to correct the arrhythmia. The catheter delivers energy from an external source (generator) to the tissue, generating sufficient heat to kill the tissue, which is thereafter replaced by scar tissue. In a successful ablation procedure, the lesions formed interrupt the electrical pathways that cause the arrhythmia so that heart rhythm is improved or returns to normal.

SUMMARY OF THE INVENTION

The present invention provides a deflectable split tip catheter for mapping electrical pathways in the heart and for delivering RF energy to ablate heart tissue to interrupt aberrant electrical pathways. The catheter comprises an elongated catheter body, a tip section at the distal end of the catheter body and a control handle at the proximal end of the catheter body. A split tip electrode, comprised of a plurality of electrode members, is carried at the distal end of the tip section. Means are provided for securing the split tip electrode to the tip section. Means are also provided for passing a fluid through at least one member of the split tip electrode. Means are further provided for controllably deflecting the tip section. Preferably, means are also provided for monitoring the temperature of each electrode member.

The elongated body of the catheter comprises at least one lumen, preferably a central lumen through which a plurality of electrode lead wires, an infusion tube and at least one puller wire may extend. The tip section comprises a section of flexible tubing having at least one lumen, including preferably at least one off-axis lumen, and more preferably multiple lumens including at least one off-axis lumen, through which an infusion tube, electrode lead wires and at least one puller wire may extend.

The split tip electrode is formed in whole or in part by an assembly of distal electrode members (referred herein as a distal electrode assembly) with or without a proximal cup electrode. The distal electrode assembly includes a distal portion with an exterior surface, preferably comprising a rounded or bullet-shaped distal end, and a proximal portion forming a recessed stem. In a preferred embodiment of the invention, the distal electrode assembly comprises four electrode members arranged symmetrically about the longitudinal axis of the tip section forming a "quad tip electrode", each member forming a quadrant of the distal electrode assembly. Each electrode member is electrically connected to an associated electrode lead wire. Each electrode member is separated from other electrode members by insulation or the like.

A preferred split tip electrode comprises a cup electrode having a distal cylindrical portion which forms a ring electrode and a proximal portion forming a recessed stem. The cup electrode is hollow for receiving and securing therein the recessed stem of the distal electrode assembly. The cup electrode is electrically isolated from the electrode members of the distal electrode assembly. The cup electrode may be secured directly to the flexible tubing of the tip section or to a short section of a generally rigid plastic bridge tubing which receives at its distal end the recessed stem of the cup electrode. In the latter embodiment, the bridge tubing receives at its proximal end, a recessed distal end of the flexible tubing of the tip section.

A split tip electrode comprising a distal electrode assembly without a cup electrode may be connected to the tip section tubing by means of a generally hollow section of bridge tubing made of a generally rigid material that will not deform as a result of temperatures reached during an ablation procedure. The bridge tubing receives at its distal end at least a portion of the recessed stem of the distal electrode assembly and at its proximal end, a recessed distal end of the tip section tubing. If desired, one or more ring electrodes may be carried on the bridge tubing and/or on the tip section tubing.

A preferred means for passing a fluid through one or more electrode members of the tip electrode assembly comprises an infusion tube that extends through the catheter body and tip section and into a passageway, preferably an axial passageway, in the tip electrode assembly. The passageway extends from the proximal end of the composite tip electrode a portion of the distance to the distal end where the passageway branches into one or more generally transverse channels which extend(s) through at least one, and preferably each, of the electrode members. Rather than having one or more generally transverse channels in each electrode member, one or more electrode members may be made of a porous material through which fluid from an infusion tube may pass.

DETAILED DESCRIPTION OF THE INVENTION

A preferred embodiment of an irrigated split tip electrode catheter constructed in accordance with the present invention is shown in FIGS. 1–6. The catheter 10 comprises an elongated catheter body 11 and a tip section 12 at the distal end of the catheter body 11 and a control handle 13 at the proximal end of the catheter body 11.

Figure 1:
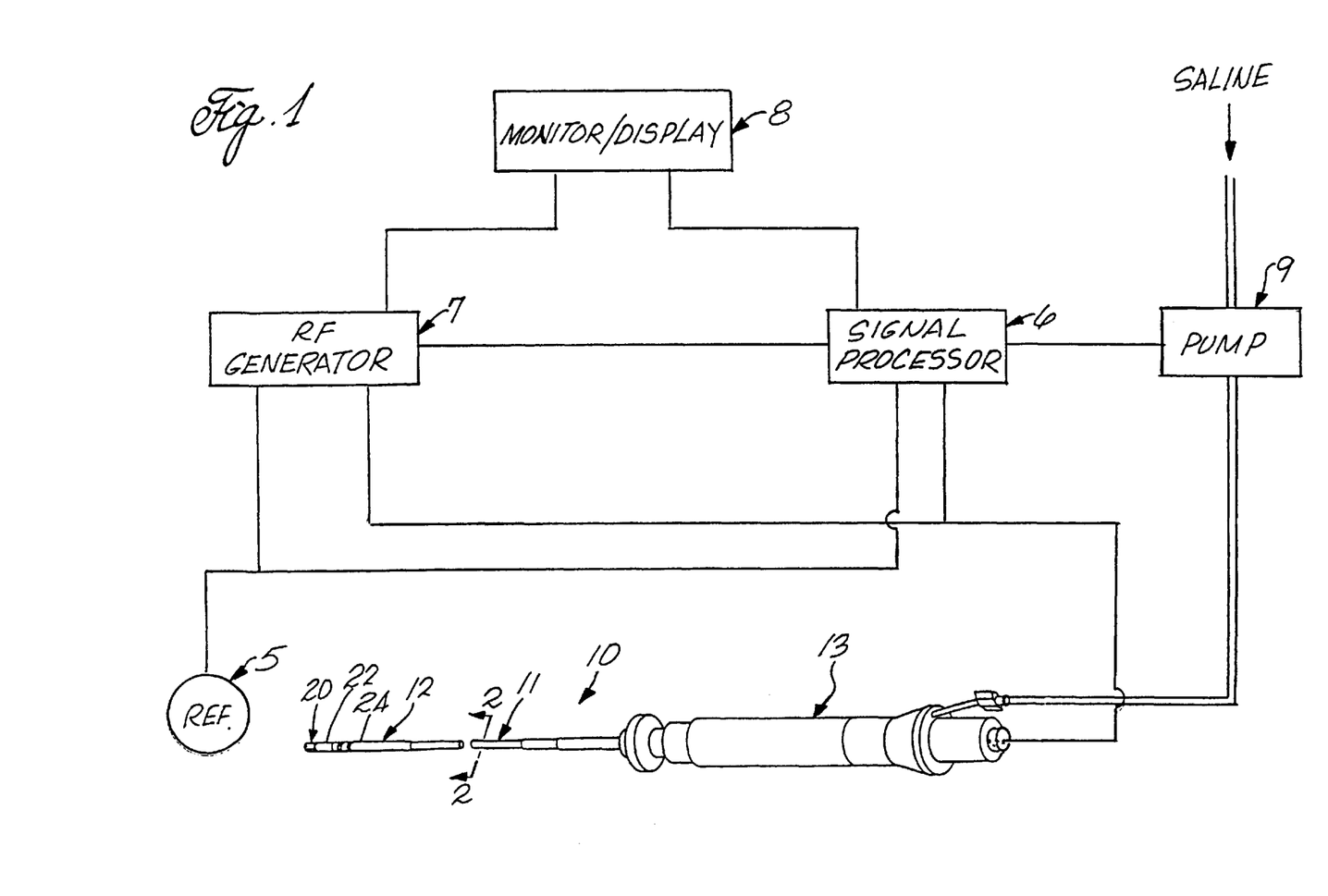
FIG. 1 is a perspective view of the irrigated split tip electrode catheter of FIG. 1.
Figure 2:
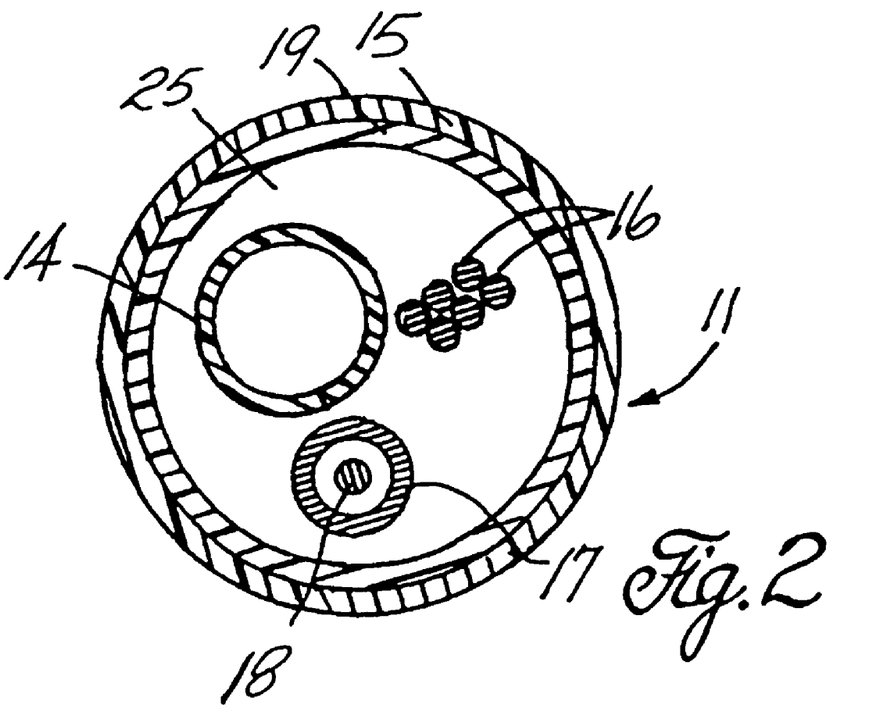
FIG. 2 is a transverse cross-sectional view of the catheter body along line 2—2 in FIG. 1.

With reference to FIG. 2, the catheter body 11 comprises an elongated tubular construction having a single, central or axial lumen 25. The catheter body 11 is flexible, i.e., bendable, but substantially non-compressible along its length. The catheter body 11 can be of any suitable construction and made of any suitable material. A presently preferred construction comprises an outer wall 15 made of a polyurethane or the like and an inner stiffening tube 19. The outer wall comprises an imbedded braided mesh of stainless steel or the like to increase torsional stiffness of the catheter body 11 so that, when the control handle 13 is rotated, the tip section of the catheter 10 will rotate in a corresponding manner. The outer diameter of the catheter body 11 is not critical, but is preferably no more than about 8 french. Likewise the thickness of the outer wall is not critical.

The inner surface of the outer wall is lined with a stiffening tube 19, which can be made of any suitable material, preferably polyimide. The stiffening tube 19, along with the braided outer wall 15, provides improved torsional stability while at the same time minimizing the wall thickness of the catheter, thus maximizing the diameter of the single lumen. The outer diameter of the stiffening tube 19 is about the same as or slightly smaller than the inner diameter of the outer wall. Polyimide tubing is presently preferred because it may be very thin walled while still providing very good stiffness. This maximizes the diameter of the central lumen without sacrificing strength and stiffness.

A particularly preferred catheter body 11 has an outer wall with an outer diameter of about 0.092 inch and an inner diameter of about 0.063 inch and a polyimide stiffening tube having an outer diameter of about 0.061 inch and an inner diameter of about 0.052 inch.

As shown in FIG. 2, extending through the lumen are an infusion tube 14, a plurality of electrode lead wires 16, having an insulation coating, and a compression coil 17 in surrounding relation to a puller wire 18.

Figure 3:
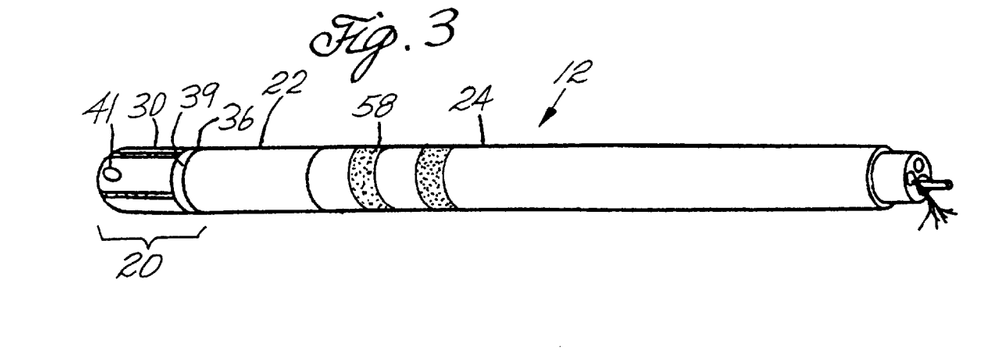
FIG. 3 is a perspective view of the tip section of the preferred irrigated split tip electrode catheter of FIG. 1.
Figure 4:
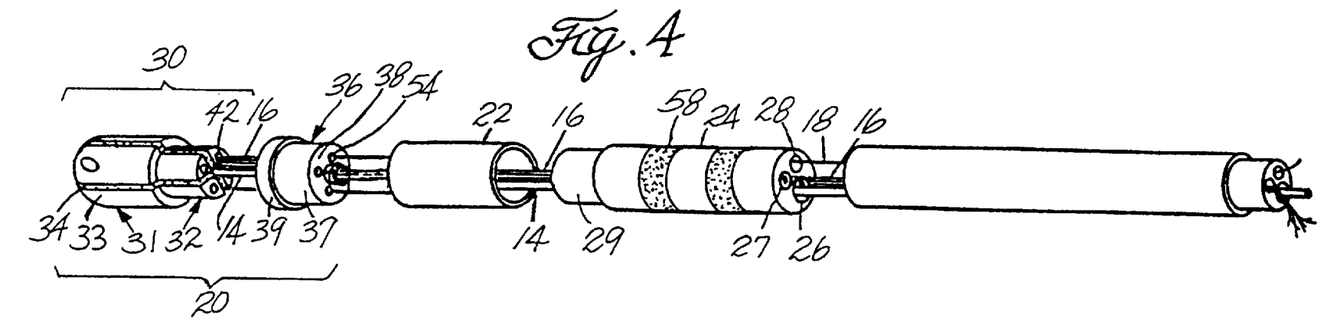
FIG. 4 is an exploded perspective view of the tip section of the preferred irrigated split tip electrode of FIG. 1.

An enlarged side view of the tip section 12 is shown in FIGS. 3 and 4. The tip section comprises a split tip electrode 20 comprising a "quad" tip electrode, i.e. a four member tip electrode assembly 30 and a cup electrode 36. The tip section 12 further comprises a bridge tubing 22 and a section of flexible tubing 24. The tubing 24 is made of a suitable non-toxic material which is preferably more flexible than the catheter body 11. A presently preferred material for the tubing 24 is braided polyurethane, i.e., polyurethane with an embedded mesh of braided stainless steel or the like. The outer diameter of the tip section 12, like that of the catheter body 11, is preferably no greater than about 8 french. The proximal end of the flexible tubing 24 is attached to the distal end of the catheter body 11 by any suitable means.

In the embodiment shown, the flexible tubing 24 has three off axis lumens, a first lumen 26 through which the infusion tube 14 extends, a second lumen 27 through which the electrode lead wires 16 extend and a third lumen 28 through which the puller wire 18 extends. The diameter of the three lumens may be the same or may differ a desired. The presently preferred diameters of the first, second and third lumens are about 0.035 inch, about 0.022 inch and about 0.022 inch. The length of the flexible tubing is not critical but is preferably about 2 to 3 inches. The distal end of the flexible tubing is recessed or stepped down to form a distal stem 29 which fits into the proximal end of the bridge tubing 22.

With reference to FIG. 4, the quad tip electrode 30 has a distal portion 31 having an exterior surface with a preferably rounded or bullet shaped distal end, and a proximal portion 32 which forms a recessed stem. The outer diameter of the distal portion 31 is preferably 8 french or less. The overall length of the distal portion is not critical but is sufficient for ablation. A presently preferred length is about 2.5 mm.

The quad tip electrode 30 comprises a four electrode members 33. Each electrode member 33 comprises a pair of flat interior surfaces and an exterior surface. The electrode members 33 are arranged with each flat side of each electrode member adjacent to a flat side of another electrode member, separated therefrom by insulation 34, preferably high-temperature epoxy. To facilitate the connection of electrode and lead wires 16, each electrode member 33 further comprises an electrode lead bore 42 in its proximal end generally parallel to the axis of the catheter body 11.

Each of the electrode members 33 can be of any suitable construction and is preferably made of platinum. It is understood that the number, shape and various dimensions of the electrode members 33 are not critical and may be varied as desired.

The cup electrode 36 is hollow and comprises a generally cylindrical side wall 37 and a generally flat proximal end wall 38. The distal portion of the side 37 wall has an exterior surface 39 forming a ring electrode. The proximal portion of the side wall 37 is recessed. The stem 32 of the quad tip electrode 30 is received and secured within the hollow interior of the cup electrode 36, by polyurethane glue or the like which electrically insulates the composite tip electrode 30 from the cup electrode 36.

Figure 5:
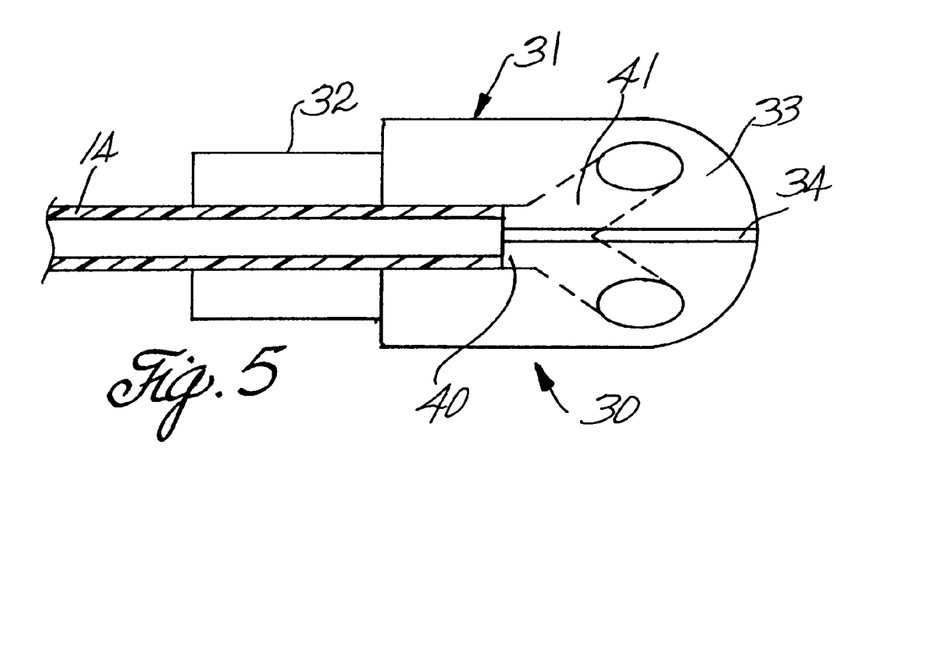
FIG. 5 is a side view of the split tip electrode of the catheter of FIG. 1.

The quad tip electrode 30 comprises a central irrigation channel 40, formed, for example by drilling, for receiving the distal end of the infusion tube 14. The central irrigation channel 40 extends axially from the proximal end of the quad tip electrode 30 to about the midpoint of the quad tip electrode 30. There, the channel 40 divides into four generally transverse branches 41, each branch extending distally and radially, e.g., at a 45° angle, through a separate electrode member 33. The diameters of the central channel 40 and branches 41 are not critical. A presently preferred composite tip electrode has a central irrigation channel 40 having a diameter of about 0.5 mm and four branches 41, each having a diameter of about 0.4 mm.

It is to be understood that the size and number of channels and/or branches may vary as desired. For example, each electrode member may have a plurality of branches rather than a single branch. Each branch may comprise secondary branches if desired. Rather than defined branches, the electrode members may be made of a porous material, e.g. as described in U.S. Pat. Nos. 5,643,197, and 5,462,521, which are incorporated herein by reference.

If desired, less than all of the electrode members may have irrigation branches or channels. For example, if only one or two of the electrode members 33 are intended for delivering RF energy during an ablation procedure, it may be desired that only those electrode members 33 comprise irrigation branches or channels.

The cup electrode 36 comprises a plurality of pass-through bores 54 for allowing insulated electrode lead wires 16 for each of the electrode members 33 of the quad tip electrode 30 to pass through the proximal end wall 38 of the cup electrode 36 when the electrode catheter is fully assembled. Each of the pass-through bores 54 are generally parallel to the axis of the catheter body 11, are aligned with an associated electrode lead bore 42, and are equally spaced about the proximal end of the cup electrode 36. To further insulate the cup electrode 36 from the quad tip electrode 30, each of the pass-through bores 54 has a meniscus insulator with a hole defined therethrough, as shown and described in U.S. patent application Ser. No. 08/726,380 to Webster, Jr., which is incorporated herein by reference. The meniscus insulator precludes the electrical contact of the associated electrode lead wire 16 with the cup electrode 36.

In the embodiment shown, the cup electrode 36 further comprises an axial hole with a proximally extending cylindrical flange 51 around the hole. The distal portion of the infusion tube 14 extends through the flange 51 and axial hole and into the central irrigation channel 40 of the quad tip electrode 30 where it is fixedly secured by polyurethane glue or the like.

Figure 6:
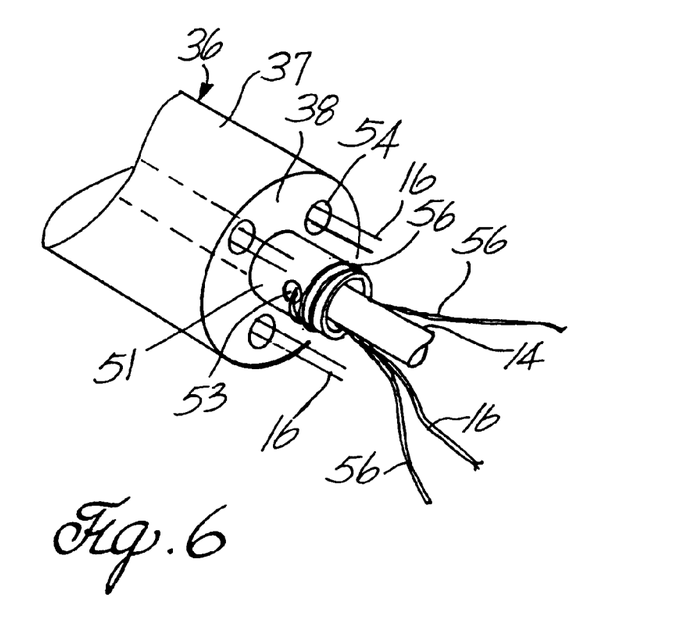
FIG. 6 is a cut-away perspective view of the proximal portion of the composite electrode of the catheter of FIG. 1 showing the connection of the electrode lead and safety wires.

The flange 51 has a transverse hole 53 at about its mid-point. An electrode lead wire 16 and a pair of safety wires 56 are fixedly attached to the stem 51 of the cup electrode 36. A preferred method of attaching the electrode lead wire 16 and safety wires 56 is shown in FIG. 6. The electrode lead wire 16 and safety wires 56 are inserted into the flange 51, passed out through the hole 53 and wrapped, preferably one and one-half times, around the flange 51. They are then soldered into place. The proximal end of the safety wires may be secured e.g. by polyurethane glue or the like anywhere in the tip section 12 proximal to the bridge tubing 22.

The cup electrode 36 can be of any suitable construction and is preferably made of platinum. The dimensions of the cup electrode are not critical. In a presently preferred errbodiment, the length of the cup electrode 33 is about 0.13 inch, the depth of the cavity 50 is about 0.08 inch, the outer diameter about 0.09 inch with a cavity diameter of about 0.08 inches.

The bridge tubing 22 is made of a short section of rigid tubular plastic, preferably PEEK (polyetheretherketone), and has an outer diameter about the same as the outer diameter of the distal portion of the quad tip electrode 30 and flexible tubing 24 of the tip section 12 and an inner diameter about the same as the recessed proximal portion of the cup electrode 36 and the recessed distal potion of the flexible tubing 24. The bridge tubing 22 connects the split tip electrode 20 to the flexible tubing 24. At its distal end, the bridge tubing 22 receives the recessed proximal portion of the cup electrode 36 which is secured therein by polyurethane glue or the like. At its proximal end, the bridge tubing 22 receives the recessed distal end of the flexible tubing 24 which is also secured therein by polyurethane glue or the like.

The length of the bridge tubing 22 is selected to provide a gap within the interior of the bridge tubing 22 between the proximal end of the cup electrode 36 and the distal end of the flexible tubing 24. The gap is sufficiently long to allow space for the infusion tube 14 to bend or curve from the off-axis lumen 26 in the flexible tubing 24 into alignment with the axial hole and flange 51 in the cup electrode 33. The electrode lead wires 16 extend out of off-axis lumen 27 in the flexible tubing 24 to separate pass-through bores 54 in the cup electrode 36 and to the flange 51 of the cup electrode 33. A bridge tubing 22 having a length of about 6 to about 7 mm and providing a gap of about 1 to about 2 mm is presently preferred. It is understood that the bridge tubing may be made of any suitable, generally rigid plastic which can withstand the temperature reached during an ablation procedure without significant, i.e., detrimental, deformation.

Figure 7:
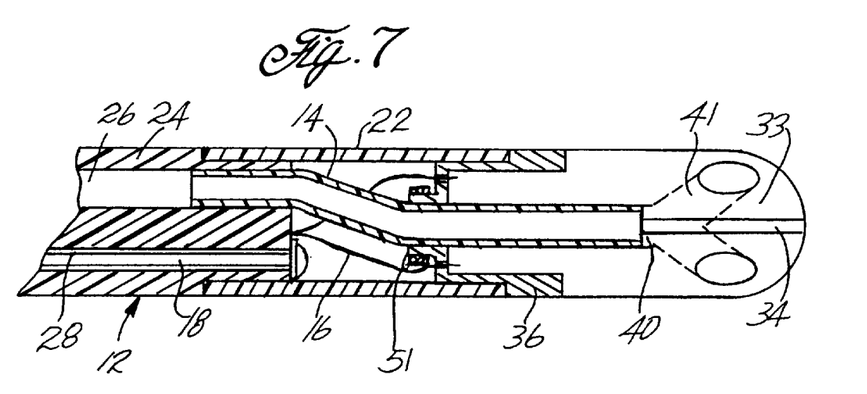
FIG. 7 is a longitudinal cross-sectional view of the catheter tip section of the embodiment of FIGS. 1 to 6 in which the infusion tube comprises two sections.

The infusion tube 14 may be made of any suitable material. Polyimide is presently preferred. It may be a single elongated tube which extends through the catheter body 11 through the first lumen 26 of the tip section 12, though the bridge tubing 22 and cup electrode 36 and into the irrigation channel 40 of the quad tip electrode. Alternatively, as shown in FIG. 7, the infusion tube 14 may comprise two sections, a proximal section which extends through the catheter body 11 and into the proximal end of the first lumen 26 of the tip section, the distal end of the proximal infusion tube section being secured in the first lumen 26 by polyurethane glue or the like. A second section of the infusion tube extends from the distal end of the first lumen 26 of the tip section 12, where it is secured by polyurethane glue or the like through the bridge tubing 22 and flange 51 of the cup electrode 36 and into the central irrigation channel 40 of the quad tip electrode.

The proximal end of the infusion tube 14 extends out of a sealed opening in the side wall of the catheter body and terminates in a Luer hub or the like. Alternatively, the infusion tube 14 may extend through the control handle 13 and terminate in a luer hub or the like at a location proximal to the handle. In either such arrangement, fluids, e.g., saline may be introduced into and passed through the infusion tube 14 and into and through the electrode members 33 of the composite tip 30 to cool the electrode members 33 during an ablation procedure. It is understood that other fluids, e.g., drugs, may also be passed through the infusion tube and out composite tip if desired. In a particularly preferred embodiment, the infusion tube is made out of thin walled polyamide tubing. It is understood that any suitable material may be used. Preferably having an outer diameter about the same as or slightly smaller than the diameter of the first lumen 26 of the tip section 12.

In a preferred embodiment, the electrode lead wires 16 associated with each electrode member 33 of the composite tip electrode 36 and cup electrode 36 is one wire of a pair of wires of dissimilar metals. The presently preferred wire pair is an enameled copper constantan wire pair comprising a copper wire, having a thickness of about 0.003" and a constantan/wire, having a thickness of about 0.003", enameled to the copper wire. Such an enameled wire pair is described in U.S. Pat. No. 5,893,885 to Webster, Jr. which is incorporated herein by reference. In this configuration, the constantan wire, which has high strength supports the copper wire which is soft and fragile. Because the leads are constructed out of two different types of wire, the leads also serve as a thermocouple for measuring the temperature of the electrode. It is understood that any temperature monitoring means, e.g., a themistor, a wire pair used exclusively as a thermocouple, may be used as desired. The leads 16 may also be used to interrupt power delivery in case of irrigation failure. The leads 16 extend into the electrode lead bores 42 of the electrode members 33 and are fixedly attached thereto by any suitable means, e.g., soldering or welding.

If desired, the irrigated split tip catheter of the present invention may comprise one or more ring electrodes 58 as shown, for example in FIG. 3. Attachment of electrode lead wires to such ring electrodes may be accomplished by any suitable means and/or procedure. A presently preferred procedure for attaching electrode leads to a ring electrode is described in U.S. patent U.S. Pat. No. 5,893,885 to Webster, Jr.

The puller wire 18 extends from the control handle 13 through the lumen 20 of the catheter body 11 and into the third off axis lumen 28 of the flexible tubing 24 of the tip section 12. The puller wire 18 is made of any suitable metal, such as stainless steel or Nitinol, and is preferably coated with Teflong or the like. The coating imparts lubricity to the puller wire 18. The puller wire 18 preferably has a diameter ranging from about 0.006 to about 0.010 inches. The distal end of the puller wire 18 is anchored at or about the distal end of the flexible tubing 24 by any applicable means. Briefly, the puller wire 18 comprises a T-bar anchor which is fixedly attached to the distal end of the puller wire. The crossbar of the T-bar anchor lies outside of the distal end of the third off-axis lumen of the flexible tubing or in a notch created in the side wall of the flexible tubing which communicates with the third lumen. The size of the crossbar is selected so that it cannot be pulled into the third lumen. In this arrangement pulling on the puller wire results in deflection of the flexible tubing of the tip section in the direction of the third lumen. It is understood that the T-bar anchor may be secured in the notch in the side wall of the tip section tubing, if desired. Alternatively, the puller wire may be soldered or welded to the cup electrode.

To prevent deflection of the catheter body when the puller wire is pulled, there is provided a compression coil 17 in surrounding relation to the portion of the puller wire extending through the catheter body. The compression coil 17 extends from the proximal end of the catheter body 11 to the distal end of the catheter body 19 or the proximal end of the tip section 12. The compression coil 17 may be made from any suitable material, but is preferably made from stainless steel. The compression coil 17 is tightly wound on itself to provide flexibility, i.e., bending, but to resist compression. The inner diameter of the compression coil is slightly larger than the diameter of the puller wire. For example, when the puller wire 18 has a diameter of about 0.007 inches, the compression coil 17 preferably has an inner diameter of about 0.008 inches. The Teflon® coating of the puller wire 18 allows it to slide freely within the compression coil 17. Along its length, the outer surface of the compression coil is covered by a flexible, nonconductive sheath to prevent contact between the compression coil 17 and any of the lead wires 16. A nonconductive sheath made of polyimide tubing is presently preferred. Such an arrangement involving a compression coil in surrounding relation to a puller wire is described in U.S. Pat. No. 5,935,124 which is incorporated fully herein by reference.

The compression coil 17 is preferably anchored at its proximal end to the proximal end of the stiffening tube in the catheter body 11 by a glue joint and at its distal end to the distal of the catheter body 11 or the proximal end of the tip section 12, by another glue joint. Both glue joints are preferably comprised of polyurethane glue or the like.

Longitudinal movement of the puller wire is controlled by control handle 13. The control handle may be of any suitable design. A presently preferred control handle for a single puller wire is disclosed in U.S. Pat. No. Re 34,502 to Webster, Jr. which is incorporated herein by reference. Such a handle is particularly applicable if the proximal end of the infusion tube extends out of the catheter body terminating in a Luer hub or the like. Alternatively, if the infusion tube extends through the control handle, a control handle as described in U.S. patent application Ser. No. 08/924,339, which is incorporated hereby by reference, is preferred.

Figure 8:
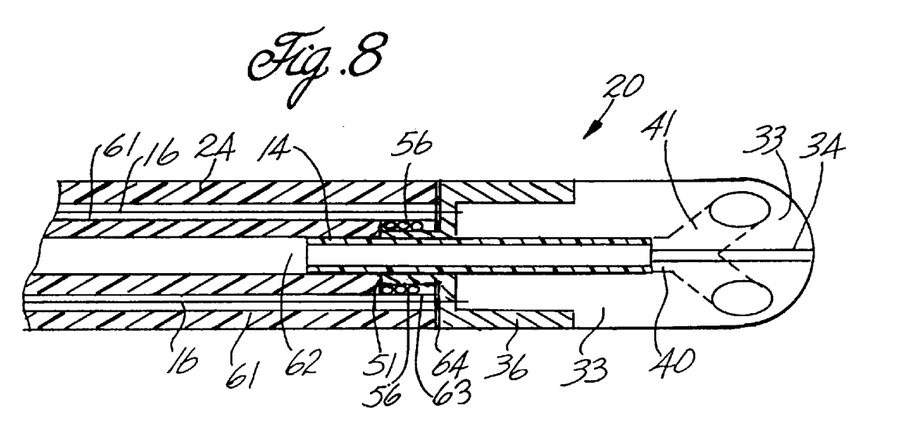
FIG. 8 is a longitudinal cross-sectional view of a tip section of a preferred embodiment of the invention which does not comprise a bridge tubing.
Figure 8A:
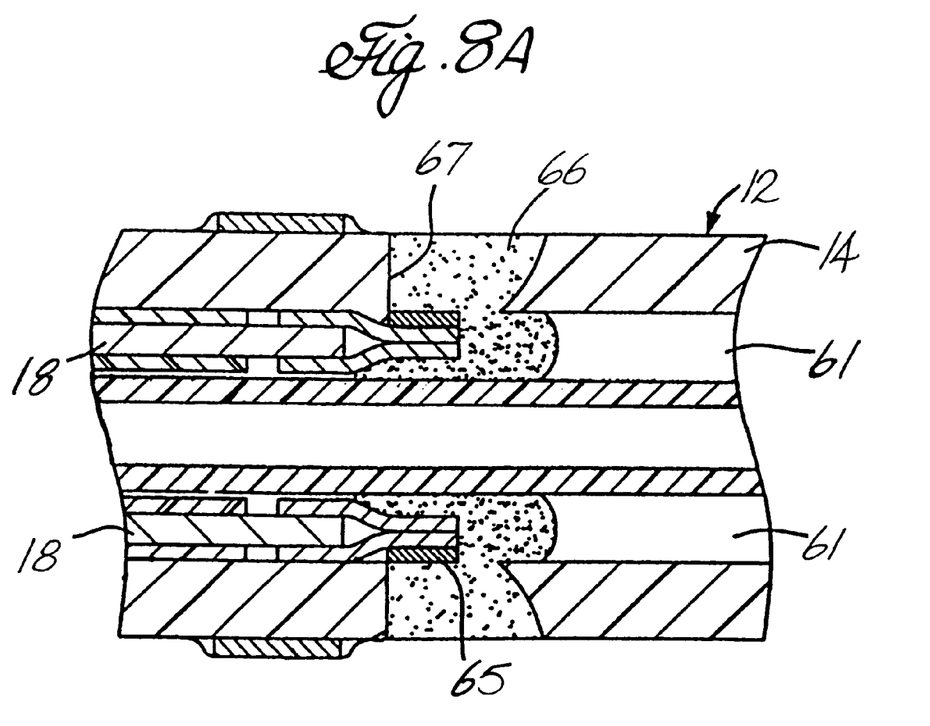
FIG. 8A is a longitudinal cross-sectional view of a portion of the tip section of FIG. 8 showing a preferred means for anchoring puller wires to the side wall of the tubing of the tip section.

In another embodiment of the invention as shown in FIG. 8 and FIG. 8A, the tip section 12 comprises split tip electrode 20 which is attached directly to the flexible tubing 24. That is, there is no bridge tubing. In this embodiment, the split tip electrode comprises a quad tip electrode as described above. The cup electrode 36 comprises a cylindrical side wall having an exterior surface forming a ring electrode. However, in this embodiment, there is no recessed proximal portion of the sidewall. That is, the entire sidewall of the cup electrode 36 forms a ring electrode.

The flexible tubing 24 comprises five lumens, 4 symmetrically spaced off-axis lumens 61 and an axial lumen 62. The flexible tubing 24 comprises an axial bore 63 at its distal end having a diameter slightly larger than the outer diameter of the cylindrical flange 51 of the cup electrode 36 to accommodate the safety wires 56 and cup electrode lead wire 16 which is wrapped around the outer circumference of the cylindrical flange 51. If desired, the distal ends of the safety wires 56 may be flattened to reduce the diameter of the trepanned hole 63 in the flexible tubing 24 needed to accomodate the cylindrical flange 51 and safety wires 56 wrapped thereabout.

The infusion tube 14 extends through the axial lumen 62 of the flexible tubing 24, through the flange 51 of the cup electrode 36 and directly into the central irrigation channel 40 of the quad tip electrode. As described above, the infusion tube may be a single elongated tube or may comprise discrete proximal and distal sections.

The electrode lead wires 16, preferably enameled wire pairs as described above, for the electrode members 33 of the quad tip electrode extends through one (or more) of the off-axis lumens 62. A small gap 64 is provided between the distal end of the flexible tubing 24 and the proximal end plate of the cup electrode 36. Within this gap 64, the electrode lead wires 16 which are not aligned with a pass through bore in the cup electrode 36 may pass from the off-axis lumen(s) 61 to pass through bores 54 of the cup electrode 36 and then into the electrode lead bores 42 of the electrode members 33 of the quad tip electrode 30 where they are fixedly attached.

In this embodiment, there are two puller wires 18 which extend through the catheter body 11 and into diametrically opposed off-axis lumens 61 in the flexible tubing 24. The distal ends of the puller wires 18 preferably comprise T-bar anchors 65 as described above and are preferably anchored by glue 66 in notches 67 in the side wall of the flexible tubing 24 as shown in FIG. 8A. Alternatively, the distal ends of the puller wires may be soldered or welded directly to the proximal end plate of the cup electrode 36.

The cup electrode 36 is fixedly secured to the distal end of the flexible tubing 24 by polyurethane glue or the like which fills the gap 64.

Figure 9:
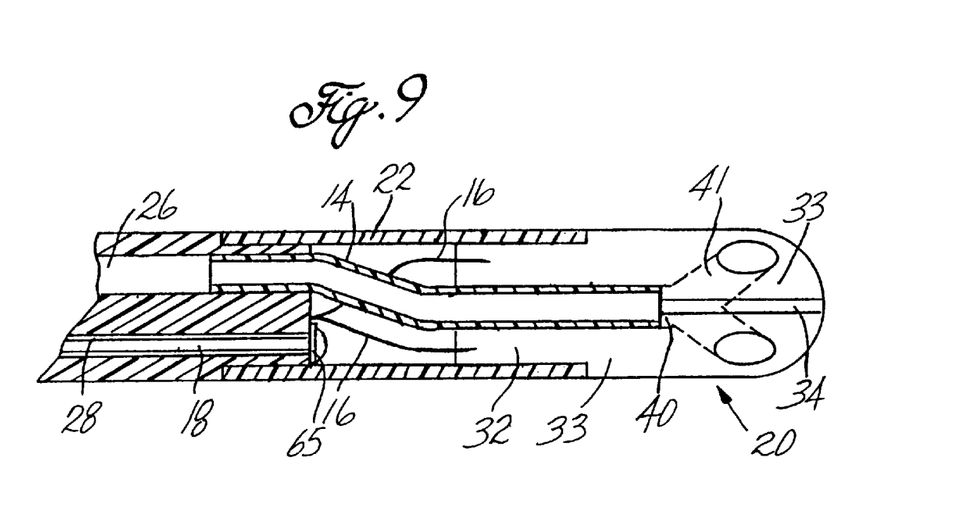
FIG. 9 is a longitudinal cross-sectinal view of the tip section of a preferred embodiment of the invention in which the split tip electrode does not include a cup electrode.

In yet another embodiment of the invention shown in FIG. 9, the tip section comprises a section of flexible tubing 24, a bridge tubing 22 and the split tip electrode 20 comprises a quad tip electrode, but no cup electrode. In such an embodiment, the recessed stem 32 of the quad tip electrode extends directly into the distal end of the bridge tubing 22 and is secured therein by polyurethane glue or the like.

At its proximal end, the bridge tubing 22 receives the recessed distal end of the flexible tubing 24. The flexible tubing 24 preferably comprises three off-axis lumens, as described with respect to the embodiment of FIGS. 1–7, through which an infusion tube 14, electrode lead wires 16 and a puller wire 18 extend. It is understood that, if desired, three lumen flexible tubing 24 may be used in which all lumens are diametrically aligned. A three off-axis lumen is preferred, however, because it provides superior strength. If bidirectional capability is desired, the flexible tubing preferably comprises four off-axis lumens, and the puller wires 18 extending through diametrically opposed off-axis lumens.

Figure 10:
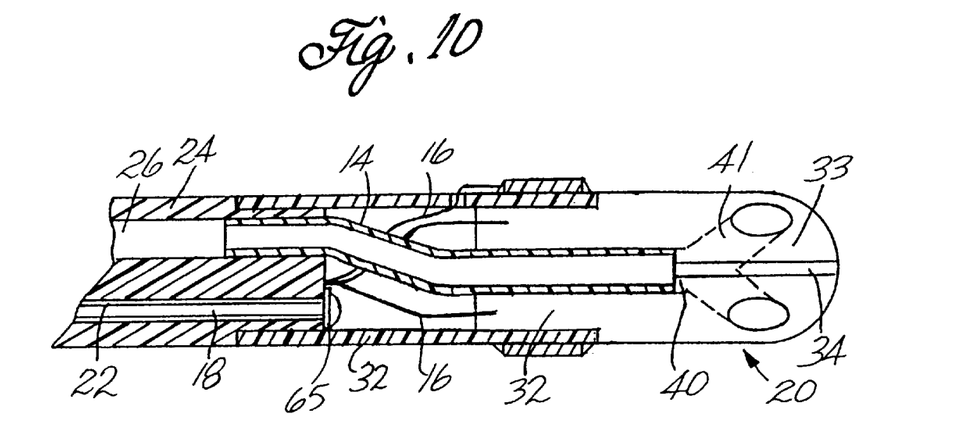
FIG. 10 is a longitudinal cross-sectional view of the tip section of another embodiment of the invention similar to FIG. 9 and including a ring electrode on the bridge tubing.

If desired, an electrically isolated ring electrode 58 may be mounted around the distal end of the bridge tubing 22 as shown in FIG. 10. In such an embodiment, the lead wire for the ring electrode extends through a small hole in the bridge tubing 22 and across the exterior surface of the bridge tubing to the electrode 58. The lead wire is covered and the hole in the bridge tubing is filled with polyurethane resin or the like. More than one ring electrodes may be carried by the bridge tubing or the flexible tubing.

Figure 11:
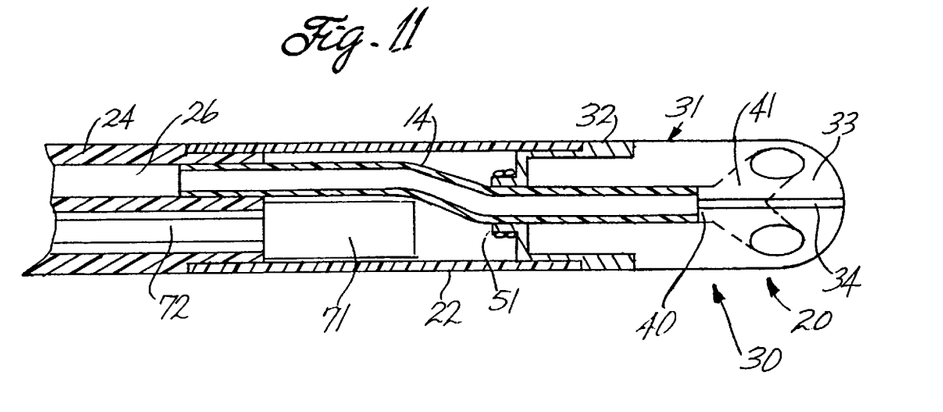
FIG. 11 is a longitudinal cross-sectional view of the tip section of another preferred embodiment of the invention including an electromagnetic sensor.

In a further embodiment of the invention as shown in FIG. 11, the tip section 12 carries an electromagnetic sensor 71 within the bridge tubing 22. In this embodiment, the split tip electrode 20 may (as shown) or may not comprise a cup electrode 36, as desired. The flexible tubing 24 comprises at least three off-axis lumens, one for a cable 72 which extends from the electromagnetic sensor 71 through the tip section 12, catheter body 11 and handle 13 to a connector for connection to a signal processing and imaging means. If desired, a circuit board can be provided in the control handle. The sensor cable is connected to the circuit board, which amplifies the signal received from the electromagnetic sensor and transmits it to a computer in a form understandable by the computer. The other two lumens in the flexible tubing are for the infusion tube 14 and electrode lead wires (not shown) and for a puller wire (not shown). Again, if bidirectional capability is desired, a fourth off-axis lumen in the flexible tubing would be required for the second puller wire. Suitable electromagnetic sensors and signal processing and imaging means are commercially available from Cordis Webster, Inc., and are described in U.S. Pat. Nos. 5,558,091, 5,443,489, 5,480,422, 5,546,951, 5,568, 809, and 5,391,199 and International Publication No. WO95/02995 which are incorporated herein by reference.

In this embodiment, the bridge tubing 22 is sufficiently long to allow the infusion tube 14. to curve around the electromagnetic sensor 71 and into the axial flange 51 of the cup electrode 36 into the central irrigation channel 40 in the quad tip electrode.

It is to be understood that, with respect to the embodiments described above comprising a single puller wire, the catheter may comprise two or more puller wires. Likewise, those embodiments described above comprising a pair of puller wires may, if desired, comprise only a single puller wire. In an embodiment comprising a pair of puller wires, the flexible tubing 24 of the tip section 12 would preferably comprise four off-axis lumens. The puller wires would preferably extend into diametrically opposed off axis lumens and be anchored at the distal end of the flexible tubing as described above. Control handles for manipulating a pair of puller wires are well known. Preferred control handles are described in U.S. Pat. No. Re 34,502 to Webster, Jr., and U.S. patent application Ser. Nos. 08/924,611, 08/982,113, and 09/143,426 to Webster, Jr., and Ser. No. 09/130,359 to Ponzi, all of which are incorporated herein by reference.

In the event that an omni-directional capability is desired, the catheter may comprise three or more, and preferably four puller wires. In such an embodiment, the flexible tubing of the tip section would preferably comprise four off-axis lumens, one in each quadrant, through which the puller wires extend. A central lumen in the tip section would preferably be provided to accommodate the infusion tube and electrode lead wires. Such an arrangement of lumens and puller wires and a control handle for manipulating the puller wires is disclosed in U.S. patent application Ser. No. 08/924,611 to Webster, Jr., which is incorporated herein by reference.

It is to be understood that any suitable means for controllably deflecting the tip section in one or more may be used. Examples of other such means can be found in U.S. Pat. No. 5,656,030 to Hunjan, et al, U.S. Pat. Nos. 5,195, 968, 5,254,088, 5336,189, 5,531,686 to Lundquist, et al, U.S. Pat. Nos. 5,273,535, 5,281,217, 5,370,678 to Edwards, et al, U.S. Pat. No. 5,358,478 to Thompson, et al, U.S. Pat. Nos. 5,364,351 and 5,456,664 to Hemzelman, all of which are incorporated herein by reference.

It is understood that any construction providing a split tip electrode comprising two or more electrode members may be used in this invention. The presence of a cup electrode, while preferred is not required. Likewise, the presence of a bridge tubing is preferred, but not required.

The irrigated split tip electrode catheter of the present invention can be used to sense, i.e., map, the electrical pathways of the heart, both speed and direction, locate aberrant pathways and to interrupt those aberrant pathways by delivering RF energy to the aberrant pathway through one or more electrode members of the composite tip electrode to ablate the tissue thereat. During ablation, the RF delivery electrode members and the interface between the electrode members and the myocardium or blood are cooled to avoid the formation of coagulum on the electrode surface by passing a fluid, e.g., saline solution, through the infusion tube and the composite tip electrode. A particularly preferred method for using the described irrigated split tip catheters is disclosed in the U.S. Patent Application No. 09/205,628 entitled Split Tip Catheter and Signal Processing RF Ablation System by Webster, Jr. , filed concurrently herewith and incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An irrigated split tip electrode catheter, comprising:
   an elongated catheter body having proximal and distal ends and at least one lumen extending therethrough;
   a catheter tip section extending from the distal end of the catheter body, the catheter tip section comprising a:
   flexible tubing having proximal and distal ends and at least one lumen therethrough;
   a split-tip electrode comprising a tip electrode assembly including at least two adjacent, electrically isolated electrode members fixedly attached at the distal end of the tip section and an irrigation channel through at least one electrode member; and
      means for fixedly connecting the split-tip electrode to the distal end of the flexible tubing;
      an electrode lead wire electrically connected to each electrode member of the tip electrode assembly, each such electrode lead wire extending through a lumen in the flexible tubing and catheter body to the proximal end of the catheter;
      an infusion tube which extends through the catheter body and tip section that is in communication with the irrigation channel of the at least one electrode member and means at the proximal end of the infusion tube for introducing a fluid into and through the infusion tube and the irrigation channel of the at least one electrode member; and
      means for controllably deflecting the tip section.

2. A catheter as recited in claim 1 wherein the tip electrode assembly further includes an axial irrigation channel which extends distally from the proximal end of the tip electrode assembly a portion of the length of the tip electrode assembly, wherein the irrigation channel through at least one electrode member comprises an irrigation channel which branches off from the axial irrigation channel and extends through the electrode member, and wherein the infusion tube is in communication with the axial irrigation channel.

3. A catheter as recited in claim 2 wherein each electrode member of the tip electrode assembly comprises an irrigation channel which branches off of the axial irrigation channel and extends through said electrode member.

4. A catheter as recited in claim 1 wherein at least one electrode member is formed from a porous material.

5. A catheter as recited in claim 1 wherein the fixedly connecting means comprises a hollow bridge tubing connecting and defining a gap between the distal end of the flexible tubing and the proximal end of the tip electrode assembly.

6. A catheter as recited in claim 1 further comprising a means for sensing the temperature of at least one electrode member.

7. A catheter as recited in claim 6 wherein the temperature sensing means comprises a wire pair associated with each electrode member of the tip electrode assembly, each said wire pair comprising a pair of wires of dissimilar metals enameled together along their length, each wire of each such wire pair extending through the catheter body and flexible tubing of the tip section and being electrically connected to its associated electrode member.

8. A catheter as recited in claim 7 wherein one wire of each wire pair functions as an electrode lead wire.

9. A catheter as recited in claim 1 wherein the catheter body comprises a single axial lumen.

10. A catheter as recited in claim 9 wherein the flexible tubing of the tip section comprises at least three off-axis lumens.

11. A catheter as recited in claim 1 wherein the tip section is controllably deflectable in at least two directions.

12. A catheter as recited in claim 1 wherein the electrode members are positioned about the axis of the electrode assembly, each electrode member having a pair of interior flat sides and an exterior contact surface, wherein each interior flat side of each electrode member is adjacent to a flat side of another electrode member and electrically isolated therefrom by a non-conductive material.

13. A catheter as recited in claim 12 wherein the tip electrode assembly comprises four electrode members, each forming a quadrant of the tip electrode assembly.

14. A catheter as recited in claim 12 wherein each electrode member has a pie-shaped cross-sectional configuration.

15. An irrigated split-tip electrode catheter for cardiac electrophysiology comprising:
   an elongated catheter body suitable for intravascular insertion having proximal and distal ends and a lumen therethrough;
   a catheter tip section extending from the distal end of the catheter body and comprising:
      a flexible tubing having at least one lumen therethrough;
      a split tip electrode at the distal end of the tip section comprising:
         a tip electrode assembly comprising a plurality of electrode members, each electrode member being adjacent on at least one side to another electrode member and separated therefrom by insulation, said tip electrode assembly including a distal portion having an external surface, a recessed proximal stem portion and at least one irrigation channel in at least one electrode member; and
         a cup electrode having a cylindrical side wall and a proximal end wall defining a cavity shaped to receive at least a portion of the recessed stem portion of the tip electrode assembly, the proximal wall comprising at least one opening for the passage of an infusion tube and electrode lead wires therethrough, said cup electrode being separated by insulation and fixedly secured to the tip electrode assembly; and
      a bridge tubing fixedly connected at its distal end to the proximal end of the split-tip electrode and at its proximal end to the distal end of the flexible tubing and providing a gap between the distal end of the flexible tubing and the proximal end of the split tip electrode;
   an infusion tube having proximal and distal ends extending through the catheter body and tip section, the distal end of the infusion tube being fixedly attached to the tip electrode assembly, the interior of the infusion tube being in communication with the at least one irrigation channel in the at least one electrode member, the proximal end of the infusion tube being adapted to receive a fluid;
   electrode lead wires having proximal and distal ends extending through the catheter body and tip section, each lead wire being associated with and electrically connected to a separate electrode member or cup electrode,
   means for controllably deflecting the tip section.

16. A catheter as recited in claim 15 wherein the tip electrode assembly comprises four electrode members.

17. A catheter as recited in claim 15 wherein the tip electrode assembly further includes a central irrigation channel coaxial with and extending from the proximal end of the tip electrode assembly at least a portion of the length therethrough, and wherein the at least one irrigation channel in the at least one electrode member comprises a branched irrigation channel therethrough in communication with the central irrigation channel.

18. A catheter as recited in claim 15 wherein at least one electrode member is porous and the irrigation channel comprises the pores of the porous electrode member.

19. A catheter as recited in claim 15 further comprising means for monitoring the temperature of at least one of the electrode members of the tip electrode assembly.

20. A catheter as recited in claim 15 wherein the electrode members are positioned about the axis of the electrode assembly, each electrode member having a pair of interior flat sides and an exterior contact surface, wherein each interior flat side of each electrode member is adjacent to a flat side of another electrode member and electrically isolated therefrom by a non-conductive material.

21. A catheter as recited in claim 20 wherein each electrode member has a pie-shaped cross-sectional configuration.

22. An irrigated split tip electrode catheter, comprising:
an elongated catheter body having proximal and distal ends and a single lumen extending therethrough;
a catheter tip section extending from the distal end of the catheter body, the catheter tip section comprising a:
flexible tubing having proximal and distal ends and at least three lumens therethrough;
a split-tip electrode comprising a tip electrode assembly including at least two adjacent, electrically isolated electrode members fixedly attached at the distal end of the tip section; and
means for fixedly connecting the split-tip electrode to the distal end of the flexible tubing;
an electrode lead wire electrically connected to each electrode member of the tip electrode assembly, each such electrode lead wire extending through a lumen in the flexible tubing and catheter body to the proximal end of the catheter;
means for passing a fluid through the catheter body, tip section and at least one electrode member of the tip electrode assembly; and
means for controllably deflecting the tip section.

23. A catheter as recited in claim 22 wherein the means for passing a fluid through the catheter body, tip section and at least one electrode member of the tip electrode assembly comprises an infusion tube which extends through the catheter body and tip section, an irrigation channel through at least one electrode member of the tip electrode assembly, said channel being in communication with the infusion tube, and means at the proximal end of the infusion tube for introducing a fluid into and through the infusion tube and the irrigation channel of the at least one electrode member.

24. A catheter as recited in claim 23, wherein the tip electrode assembly further includes an axial irrigation channel which extends distally from the proximal end of the tip electrode assembly a portion of the length of the tip electrode assembly, wherein the irrigation channel through at least one electrode member comprises an irrigation channel which branches off from the axial irrigation channel and extends through the electrode member and wherein the infusion tube is in communication with the axial irrigation channel.

25. A catheter as recited in claim 24 wherein each electrode member of the tip electrode assembly comprises an irrigation channel which branches off of the axial irrigation channel and extends through said electrode member.

26. A catheter as recited in claim 22 wherein at least one electrode member is formed from a porous material.

27. A catheter as recited in claim 22 wherein the fixedly connecting means comprises a hollow bridge tubing connecting and defining a gap between the distal end of the flexible tubing and the proximal end of the tip electrode assembly.

28. A catheter as recited in claim 22 further comprising a means for sensing the temperature of at least one electrode member.

29. A catheter as recited in claim 28 wherein the temperature sensing means comprises a wire pair associated with each electrode member of the tip electrode assembly, each said wire pair comprising a pair of wires of dissimilar metals enameled together along their length, each wire of each such wire pair extending through the catheter body and flexible tubing of the tip section and being electrically connected to its associated electrode member.

30. A catheter as recited in claim 29 wherein one wire of each wire pair functions as an electrode lead wire.

31. A catheter as recited in claim 22 wherein the tip section is controllably deflectable in at least two directions.

32. A catheter as recited in claim 22 wherein the electrode members are positioned about the axis of the electrode assembly, each electrode member having a pair of interior flat sides and an exterior contact surface, wherein each interior flat side of each electrode member is adjacent to a flat side of another electrode member and electrically isolated therefrom by a non-conductive material.

33. A catheter as recited in claim 32 wherein the tip electrode assembly comprises four electrode members, each forming a quadrant of the tip electrode assembly.

34. A catheter as recited in claim 32 wherein each electrode member has a pie-shaped cross-sectional configuration.

* * * * *